US009320885B2

(12) United States Patent
Vasapollo

(10) Patent No.: US 9,320,885 B2
(45) Date of Patent: Apr. 26, 2016

(54) DUAL-PURPOSE SLEEP-WEARABLE HEADGEAR FOR MONITORING AND STIMULATING THE BRAIN OF A SLEEPING PERSON

(71) Applicant: Curzio Vasapollo, Tokyo (JP)

(72) Inventor: Curzio Vasapollo, Tokyo (JP)

( * ) Notice: Subject to any disclaimer, the term of this patent is extended or adjusted under 35 U.S.C. 154(b) by 0 days.

(21) Appl. No.: 14/289,269

(22) Filed: May 28, 2014

(65) Prior Publication Data

US 2015/0343196 A1 Dec. 3, 2015

(51) Int. Cl.
*A61N 1/00* (2006.01)
*A61N 1/04* (2006.01)
*A61N 1/36* (2006.01)

(52) U.S. Cl.
CPC ............ *A61N 1/048* (2013.01); *A61N 1/36025* (2013.01)

(58) Field of Classification Search
CPC ............................. A61N 1/3605; A61N 1/048
USPC ................................................ 607/45; 600/27
See application file for complete search history.

(56) References Cited

U.S. PATENT DOCUMENTS

| 5,507,716 | A * | 4/1996 | LaBerge et al. | 600/27 |
| 8,239,030 | B1 * | 8/2012 | Hagedorn et al. | 607/45 |
| 2012/0296390 | A1 * | 11/2012 | Nakashima et al. | 607/45 |

OTHER PUBLICATIONS

Starstim Brochure—Noninvasive Wireless TCS Neurostimulator http://www.neuroelectrics.com/sites/neuroelectrics.com/files/enobio/StartimBrochure.pdf.
tDCS Headset for Gamers http://www.foc.us/.
Muse Headband http://interaxon.ca/products.html.
Zeo Sleep Manager Mobile http://www cultofmac.com/138564/zeo-sleep-manager-mobile-its-a-scale-but-for-sleep-not-weight-review-fitness-special/.

* cited by examiner

*Primary Examiner* — Theodore Stigell
*Assistant Examiner* — Nadia A Mahmood
(74) *Attorney, Agent, or Firm* — Russ Weinzimmer & Associates, P.C.

(57) ABSTRACT

A dual purpose sleep wearable headgear for both monitoring and stimulating the brain of a sleeping person is disclosed that provides a simple to use and safe platform for wearing consumer-type dual use brain stimulation and monitoring devices during sleep. The headgear enables a user to sleep comfortably while wearing the electronics and related electrodes needed for both EEG monitoring and transcranial electrical stimulation. The headgear can accept and support a miniaturized dual use monitoring/stimulation device on the forehead or the top of the head, where the bulk of the monitoring/stimulation device will not interfere with the user's sleeping position. The headgear disclosed takes the guesswork out of electrode placement, because the electrodes are prepositioned or are easily adjustable according to a predetermined pattern of electrode placement, and are appropriately sized so as to allow comfortable transcranial stimulation without producing skin irritation, and without awakening the user.

16 Claims, 21 Drawing Sheets

DUAL-PURPOSE SLEEP-WEARABLE HEADGEAR FOR MONITORING AND STIMULATING THE BRAIN OF A SLEEPING PERSON

FIELD OF THE INVENTION

The present invention relates generally to transcranial electrical stimulation, and more particularly transcranial electrical stimulation during sleep.

BACKGROUND OF THE INVENTION

In recent years, evidence has accumulated on the efficacy of transcranial electrical stimulation, using both direct current (transcranial direct current stimulation, tDCS), alternating current (transcranial alternating current stimulation, tACS), and random current (transcranial random noise stimulation, tRNS). Direct current stimulation has the ability to selectively sensitize or desensitize a particular brain area. Alternating current has the ability to entrain brain oscillations strengthening the EEG signal spectrum in a certain frequency band. Stimulation using random noise current induces consistent excitability in the target brain region.

Direct current stimulation applied during sleep has been shown to facilitate memory consolidation.

40 Hz alternating current stimulation applied during REM sleep has been shown to induce a state of consciousness known as "Lucid Dreaming", in which the person becomes aware that he is dreaming while he is dreaming. Lucid dreaming has potential applications ranging from entertainment to treatment of PTSD and nightmares, and enhancement of athletic performance.

Many more applications of electrical brain stimulation during sleep are likely to emerge, such as reducing susceptibility to noise and possibly modulating sleep phases.

Currently there are no reports of adverse side effects from tDCS, tACS and tRNS, aside from mild itching and redness on the skin underneath the stimulation electrodes. The reason is that unlike electroconvulsive therapy, the currents used in modern brain stimulation techniques are extremely small. The stimulation is not meant to force neurons to fire in a specific pattern, but only to increase their natural likelihood to do so. The brain can be viewed as a multi-stable dynamic system which is sensitive to outside "nudges". For this reason even a small current can have an impact on the overall functioning of the brain.

Unfortunately, attempting to affect the functioning of specific areas of the brain with electrical stimulation during sleep is currently a difficult undertaking, requiring medical expertise, skilled electrode positioning and application, and the involvement of a doctor or researcher throughout the stimulation.

In transcranial electrical stimulation research, it is common to monitor the EEG signal of a patient before and after stimulation, to verify whether the stimulation has had effects on the EEG spectrum. For example, alternating current stimulation can be used to potentiate frequencies around 40 Hz, and this effect can be verified by comparing the intensity of the patient's endogenous 40 Hz EEG waves before and after stimulation.

Transcranial electrical stimulation researchers normally utilize a clinical EEG monitoring device and a separate transcranial stimulation device. Electrodes are carefully applied in predetermined positions on the subject's scalp by medical personnel. Particular care is taken to ensure low impedance of the electrodes, particularly the stimulation electrodes, so as to reduce itching and redness.

A few costly devices are now available on the medical device market that allow both EEG monitoring and stimulation. The StarStim™ by Neuroelectrics is an EEG cap with a multitude of holes onto which a large variety of types of electrodes can be mounted (for instance, Ag—AgCl EEG electrodes, or sponge-type stimulation electrodes requiring periodic application of saline solution). Mounting the correct electrode type at the correct location is the responsibility of the doctor or researcher. Further, each electrode can be electrically configured to capture the EEG signal or apply a stimulation current. The configuration is controlled by medical personnel using a computer interface. This EEG cap is not suitable for, nor intended for, use during sleep. The battery is placed on the back of the head, thereby limiting the patient's sleeping position, and—for safety reasons—the product has been engineered to have an automatic shutdown time of 1 hour, thereby precluding its use throughout a full night's sleep.

In recent years, consumer devices have emerged which allow a user to monitor his/her EEG without the supervision of a medical practitioner. Such devices typically include a headband worn around the user's head, several EEG electrodes, and a small EEG monitoring device which is either embedded in the headband or structurally and electrically connected to the headband by means of snap fasteners, such as snap connectors.

The Zeo™ headband (by Zeo, Inc.) now out of production allowed monitoring of EEG signal bands during sleep to perform sleep staging. Many other commercial EEG headbands now exist on the consumer market (such as the Muse™ by Interaxon, or the Melon™ headband), though they are generally intended for wake-time EEG monitoring.

All these consumer devices do not include circuitry for brain stimulation, and even if they did the electrodes would be incapable of safely applying electrical current stimulation to the brain.

The Foc.us™ headset is at the time of writing the only commercially available tDCS headset which can be used by a user to self deliver transcranial direct current stimulation. However it is sold for the purpose of day time stimulation. Even if it was worn during sleep, it would be of no value because it would fall off.

SUMMARY OF THE INVENTION

The headgear of the invention provides a simple to use and safe platform for wearing consumer-type dual use brain stimulation and monitoring devices during sleep.

The headgear enables a user to sleep comfortably while wearing electrodes needed for both EEG monitoring and transcranial electrical stimulation. The headgear can accept and support a miniaturized dual use monitoring/stimulation device on the forehead or the top of the head, where the bulk of the monitoring/stimulation device will not interfere with the user's sleeping position. The headgear takes the guesswork out of electrode placement, because the electrodes are prepositioned or are easily adjustable according to a predetermined pattern of electrode placement, and are appropriately sized to allow comfortable transcranial stimulation without producing skin irritation, and without awakening the user.

One general aspect of the invention is a dual purpose sleep wearable headgear for both monitoring and stimulating the brain of a sleeping person. The headgear includes: one or more flexible bands capable of being worn so as to capture the head of the sleeping person; a plurality of electrodes sized and located so as to be capable of applying electrical stimulation to the sleeping person's brain, at least some of the plurality of electrodes also being capable of acquiring an EEG signal; a plurality of electrode connectors, capable of receiving the plurality of electrodes, each electrode connector being incorporated into one of the flexible bands so as to direct the electrical stimulation to an underlying portion of the sleeping person's brain; and a plurality of interface connectors for electrically connecting an electronic circuit to the headgear, the electronic circuit being capable of both acquiring the EEG signal and applying the electrical stimulation, each interface connector being electrically connected to at least one of the plurality of electrode connectors.

In some embodiments, some interface connectors are electrically connected to at least one of the plurality of electrode connectors using one of: a wire; a conductive fabric strip; a conductive thread; and a flexible circuit board.

In some embodiments, at least one electrode of the plurality of electrodes includes at least one of: a layer of electrically conductive gel; a layer of electrically conductive fabric; a sponge-like porous body capable of retaining water; and a nanostructured conductive layer. A nanostructured layer can include carbon nanotubes, gold nanostructures, a nanoparticle layer, a fractal nanostructure.

In some embodiments, at least one of the plurality of interface connectors is one of: an electrical snap connector; or a piece of conductive Velcro®; or a magnet.

In some embodiments, at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

Another general aspect of the invention is a dual purpose sleep wearable headgear for both monitoring and stimulating the brain of a sleeping person. This headgear includes: one or more flexible bands capable of being worn so as to capture the head of the sleeping person; a plurality of electrodes sized and located so as to be capable of applying electrical stimulation to respective locations on the sleeping person's head, at least some of the plurality of electrodes also being capable of acquiring an EEG signal at the same respective locations, each electrode of the plurality of electrodes being incorporated into one of the one or more flexible bands so as to direct the electrical stimulation to an underlying portion of the sleeping person's brain; and a plurality of interface connectors for electrically connecting an electronic circuit to the headgear, the electronic circuit being capable of both acquiring the EEG signal and applying the electrical stimulation, each interface connector being electrically connected to at least one of the plurality of electrodes.

In some embodiments, some interface connectors are electrically connected to at least one of the plurality of electrodes using one of: a wire; a conductive fabric strip; a conductive thread; and a flexible circuit board.

In some embodiments, at least one electrode of the plurality of electrodes includes at least one of: a layer of electrically conductive gel; a layer of electrically conductive fabric; a sponge-like porous body capable of retaining water; and a nanostructured conductive layer.

In some embodiments, at least one of the plurality of interface connectors is one of: an electrical snap connector; or a piece of conductive hook and loop material; or a magnet.

In some embodiments, at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

Another general aspect of the invention is a dual purpose sleep wearable headgear for both monitoring and stimulating the brain of a sleeping person. This headgear includes: one or more flexible bands capable of being worn so as to capture the head of the sleeping person; a plurality of stimulation electrodes, each stimulation electrode being sized and located so as to be capable of applying electrical stimulation to an underlying portion of the sleeping person's brain; a plurality of EEG electrodes, each EEG electrode being capable of acquiring an EEG signal from an underlying portion of the sleeping person's brain; a plurality of stimulation electrode connectors, each stimulation electrode connector being capable of receiving a stimulation electrode, each stimulation electrode connector being incorporated into one of the flexible bands so as to direct the electrical stimulation to an underlying portion of the sleeping person's brain; a plurality of EEG electrode connectors, each EEG electrode connector being capable of receiving an EEG electrode, each EEG electrode connector being incorporated into one of the flexible bands so as to acquire an EEG signal from an underlying portion of the sleeping person's brain; and a plurality of interface connectors for electrically connecting an electronic circuit to the headgear, the electronic circuit being capable of both acquiring the EEG signal and applying the electrical stimulation, each interface connector being electrically connected to either a stimulation electrode connector or an EEG electrode connector.

In some embodiments, some interface connectors are electrically connected to at least one of: a stimulation electrode connector; and an EEG electrode connector, using one of: a wire; a conductive fabric strip; a conductive thread; and a flexible circuit board.

In some embodiments, at least one electrode of the plurality of electrodes includes at least one of: a layer of electrically conductive gel; a layer of electrically conductive fabric; a sponge-like porous body capable of retaining water; and a nanostructured conductive layer.

In some embodiments, at least one of the plurality of interface connectors is one of: an electrical snap connector; or a piece of conductive hook and loop material; or a magnet.

In some embodiments, at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

Another general aspect of the invention is a dual purpose sleep wearable headgear for both monitoring and stimulating the brain of a sleeping person. This headgear includes: one or more flexible bands capable of being worn so as to capture the head of the sleeping person; a plurality of stimulation electrodes, each stimulation electrode sized so as to be capable of applying electrical stimulation to the sleeping person's brain, each stimulation electrode being incorporated into one of the flexible bands so as to direct the electrical stimulation to an underlying portion of the sleeping person's brain; a plurality of EEG electrodes, each EEG electrode being capable of acquiring an EEG signal from the sleeping person's head, each EEG electrode being incorporated into one of the flexible bands so as to acquire an EEG signal from an underlying portion of the sleeping person's brain; and a plurality of interface connectors for electrically connecting an electronic circuit to the headgear, the electronic circuit being capable of both acquiring the EEG signal and applying the electrical stimulation, each interface connector being electrically connected to either a stimulation electrode or an EEG electrode.

In some embodiments, some interface connectors are electrically connected to at least one of: a stimulation electrode; and an EEG electrode, using one of: a wire; a conductive fabric strip; a conductive thread; and a flexible circuit board.

In some embodiments, at least one electrode of the plurality of electrodes includes at least one of: a layer of electrically conductive gel; a layer of electrically conductive fabric; a sponge-like porous body capable of retaining water; and a nanostructured conductive layer.

In some embodiments, at least one of the plurality of interface connectors is one of: an electrical snap connector; or a piece of conductive hook and loop material; or a magnet.

In some embodiments, at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

Another general aspect of the invention is a method for stimulating the brain of a sleeping person. The method includes: attaching a flexible headgear to the head of the sleeping person, the headgear having a plurality of electrodes, affixing a dual use EEG monitoring and electrical stimulation device to the sleep wearable headgear, electrically connecting the dual use EEG monitoring and stimulation device to the plurality of electrodes, analyzing the EEG of the sleeping person's brain so as to detect a stimulation start condition, and applying an electrical potential to two or more of the plurality of electrodes, so as to deliver an electrical current to the sleeping person's brain in response to the stimulation start condition.

In some embodiments, the stimulation signal condition is one of: a sleep phase; a period of time after entering a sleep phase; and a sleep EEG feature as in a sleep spindle.

In some embodiments, the electrode potential is variable, so as to deliver a time variable electrical current to the sleeping person's brain in response to the stimulation start condition, the time variable electrical current being one of: an alternating current, or a random noise electrical current.

In some embodiments, the magnitude of the electrical current is increased gradually so as to reduce discomfort and avoid disturbing the person's sleep.

In some embodiments, the electrical current is delivered so as to induce a lucid dream.

In some embodiments, the electrical current is an alternating current of a frequency between 30 and 50 hertz.

In some embodiments, the method also includes an electrode impedance reporting phase after the attaching a dual use EEG monitoring and stimulation device to the sleep wearable headgear, so as to allow the person to adjust the headgear or add conductive paste to the headgear's electrodes until the electrode impedance is sufficiently low for stimulation to occur safely.

In some embodiments, the stimulation start condition is not permitted to proceed when the impedance of the stimulation electrodes is too high for stimulation to occur safely.

Another general aspect of the invention is a dual purpose sleep wearable electronic headgear for both monitoring and stimulating the brain of a sleeping person. The electronic headgear includes: a dual use EEG monitoring and stimulation electronic circuit, capable of both acquiring an EEG signal and producing a stimulation current; an enclosure enclosing the electronic circuit; a flexible headgear capable of being worn so as to capture the sleeping person's head, the headgear also being capable of structurally supporting the bulk of the enclosure, so as to support the enclosure at a predetermined location on the sleeping person's head, the predetermined location being selected so as to avoid substantially interfering with the sleeping person's sleep; a device-mounted electrode, sized so as to be capable of applying electrical stimulation to the sleeping person's head, the device-mounted electrode also capable of being connected to the dual use EEG monitoring and stimulation electronic circuit; and a headgear-mounted electrode, sized so as to be capable of applying electrical stimulation to the sleeping person's head, the headgear-mounted electrode being incorporated into the headgear, or capable of being affixed to the headgear at a predetermined location, the predetermined location selected so as to direct the electrical stimulation to an underlying portion of the sleeping person's brain.

In some embodiments, the EEG signal is monitored through the device-mounted electrode and the headgear-mounted electrode.

In some embodiments, the electronic headgear further includes at least one additional device-mounted electrode or at least one additional headgear-mounted electrode.

In some embodiments, the device-mounted electrode is connected to the dual use EEG monitoring and stimulation electronic circuit using at least one of: a snap contact; and a wire connector.

BRIEF DESCRIPTION OF THE DRAWINGS

The invention will be more fully understood by reference to the Detailed Description, in conjunction with the following figures, wherein.

DETAILED DESCRIPTION OF THE INVENTION

Figure 1:
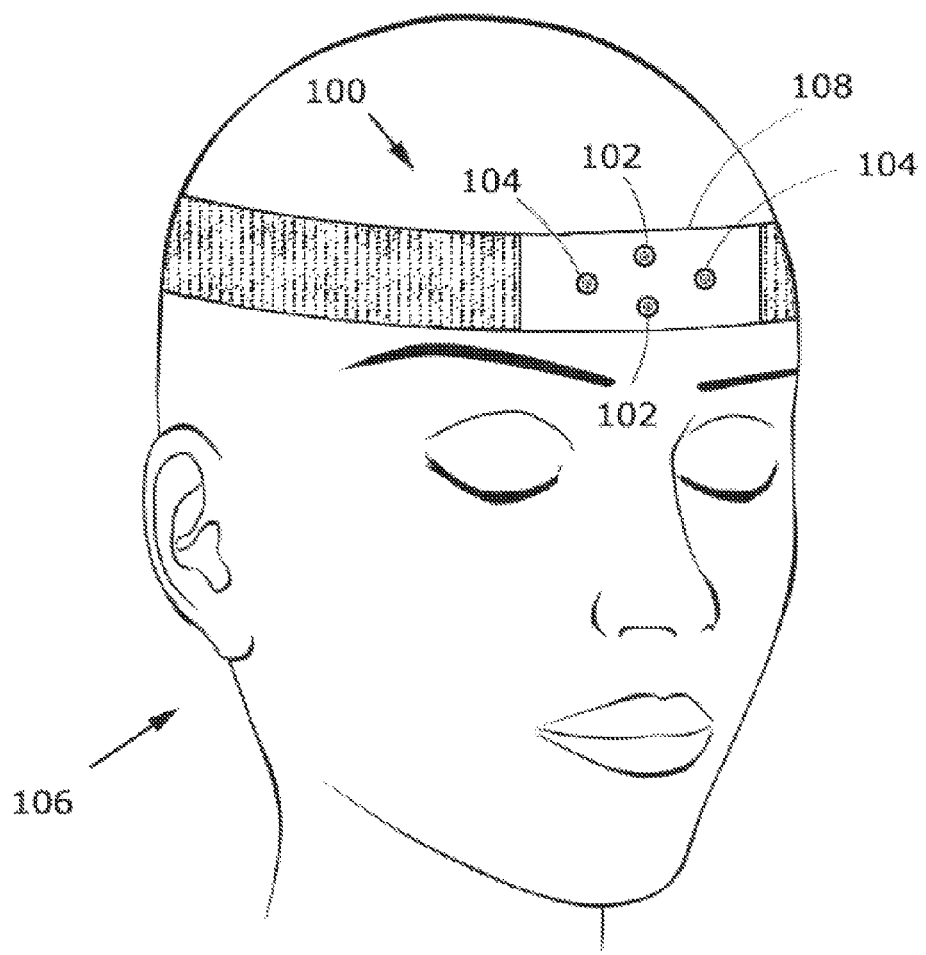
FIG. 1 is a line drawing of a person shown wearing a simple embodiment of the sleep-wearable headgear of the invention.

FIG. 1 shows a simple embodiment of the sleep-wearable headgear 100 worn by a person 106, the sleep-wearable headgear 100 essentially being a flexible band having a non-stretchable portion 108. The non-stretchable portion 108 includes two frontal interface connectors 102 and two lateral interface connectors 104. The non-stretchable portion 108 ensures that the distance between the interface connectors remains fixed even while the headgear 100 is stretching to accommodate the person's 106 head. In the embodiment shown in FIG. 1, the interface connectors are electrical snap connectors.

Figure 2A:
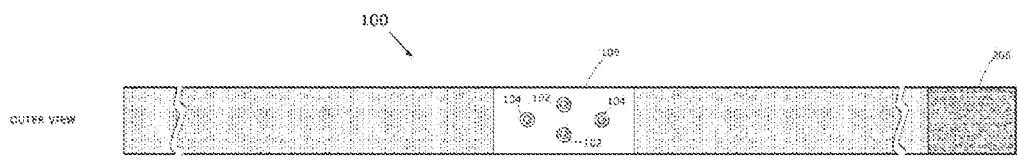
FIG. 2A and FIG. 2A' are schematic drawings of an outer view and an inner view of the sleep wearable headgear of FIG. 1.
Figure 2A:
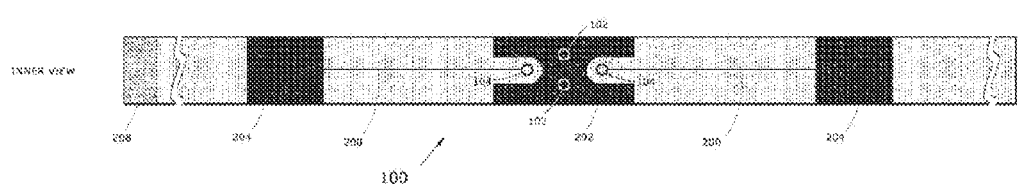

In FIG. 2A and FIG. 2A', both sides of the headgear 100 of FIG. 1 are shown in detail. When the headgear is worn, three electrodes are in contact with the person's 106 forehead: a frontal dual use electrode 202, and two lateral dual use electrodes 204. Velcro® hooks 208 and Velcro® loops 206 allow the headgear to be adjusted to fit comfortably around the person's 106 head, tightly enough to ensure good contact between the electrodes and the person's 106 forehead. Velcro® is a brand of hook and loop material, and Velcro® can refer either to the hook material, the cooperative loop material, or a combination of both. Two frontal interface connectors 102 and two lateral interface connectors 104 are located at the front of the headgear, allowing a wearable dual use brain monitoring and stimulation device 300 (such as the device shown in FIG. 3A) to be connected to and supported by the headgear.

Snap prong connectors are commonly available fasteners used in garments. They are composed of two halves, a top part and a bottom part. The bottom part includes the prongs. For each electrical snap connector labeled on the outer view (FIG. 2A), a corresponding circle is shown on the inner view (FIG. 2A'), this represents the electrically conductive bottom half of the snap connector (the prongs side).

The frontal dual use electrode 202 is electrically connected to the frontal interface connectors 102. The lateral dual use electrodes 204 are electrically connected to the lateral interface connectors 104 with two wires 200.

The electrodes 202, 204 shown in FIG. 2A and FIG. 2A' are gel electrodes, but other types of electrodes can be substituted as long as the surface area with the skin is sufficient, and the impedance of the electrodes is sufficiently low. The wires 200 can be substituted by strips of conductive fabric, conductive threads, or flexible printed circuit boards.

This embodiment allows monitoring of two EEG channels (left and right hemispheres). During monitoring, the frontal dual use electrode 202 is used as a reference electrode, while the lateral dual use electrodes 204 are used to acquire the left and right channel EEG signals.

This embodiment also allows delivery of electrical transcranial stimulation of different strengths to the left and right lobe. During stimulation, an electrical waveform of different amplitude is applied to each of the lateral dual use electrodes 204 to achieve a different stimulation strength to the left and right lobes.

Four interface connectors are not strictly required in this embodiment. The two frontal interface connectors 102 are already electrically connected and could be replaced by a single interface connector, yielding an embodiment with only three interface connectors. Further, the lateral dual use electrodes 204 could also be electrically connected, provided that a single EEG channel is sufficient for monitoring purposes, and that the strength of the electrical stimulation to be carried out is identical for both hemispheres. In this case, only two interface connectors would be necessary for both stimulation and EEG.

The electrode positioning utilized in FIG. 2A and FIG. 2A' allows a number of stimulation strategies, during both wake and sleep.

Figure 2B:
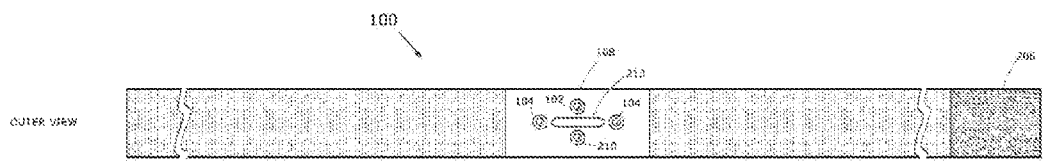
FIG. 2B and FIG. 2B' are schematic drawings of an outer view and an inner view of an alternate embodiment of the sleep wearable headgear of FIG. 1, further including a right leg drive electrode.
Figure 2B:
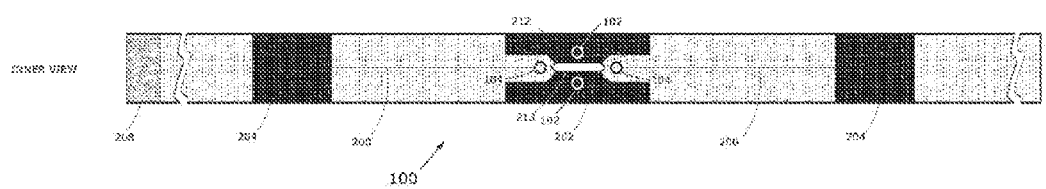

FIG. 2B and FIG. 2B' show a slightly more complex embodiment. In this figure, the headgear 100 includes a dual use right leg drive electrode 212. During EEG monitoring, the wearable dual use brain monitoring and stimulation device 300 utilizes the dual use right leg drive electrode 212 as an output to cancel the common-mode voltage and reduce noise in the EEG signal. Use of a right leg drive electrode is popular and well known in the art. During stimulation, in order to reclaim electrode surface area, the wearable dual use brain monitoring and stimulation device 300 can ensure that the dual use right leg drive electrode 212 is kept at equal electrical potential with the frontal dual use electrode 202. By so doing, the stimulation area is not decreased by the use of a right leg drive electrode. A large stimulation area minimizes the discomfort associated with electrical stimulation, and prevents unwanted awakenings when the stimulation is carried out during sleep.

The embodiment of FIG. 2B and FIG. 2B' also has a hole 213. The hole 213 enables acquisition of reflectance pulse oximetry data (including heart rate and blood oxygenation) when the wearable dual use brain monitoring and stimulation device 300 also includes a suitably located and calibrated pulse oximetry sensor 304 (shown in FIG. 3B)

In EEG monitoring, EEG signal quality is inversely proportional to the impedance of the electrodes used to acquire the EEG signal. The higher the impedance of the EEG electrodes, the lower the signal-to-noise ratio of the acquired EEG signal. Small EEG electrodes can be used as long as their impedance is low. Water gel Ag—AgCl electrodes are common in EEG recording. The sensing area is small, but their impedance is low. Electrodes for stimulation on the other hand require not only low impedance, but also a sufficiently large surface area. This is because the discomfort induced by electrical stimulation is proportional to the current density (expressed in units of current per unit surface area, for instance $mA/cm^2$). The minimum electrode surface area reported in the literature for electrical stimulation is 3.5 $cm^2$ but electrode areas of at least 12 $cm^2$ are common. Discomfort in a waking person is a simple inconvenience, but when stimulation is used to modify the characteristics of a person's sleep, discomfort can negate the benefits of the stimulation, because it can awaken the person. Therefore, for stimulation carried out during sleep, electrode size should be maximized to the extent allowed by the space available.

Figure 2C:
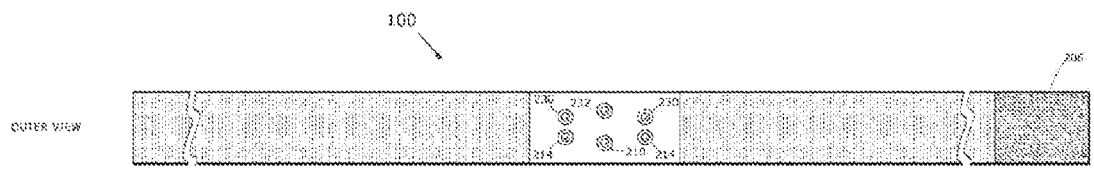
FIG. 2C and FIG. 2C' are schematic drawings of an alternate embodiment of the sleep wearable headgear of the invention, this embodiment including both EEG electrodes and stimulation electrodes.
Figure 2C:
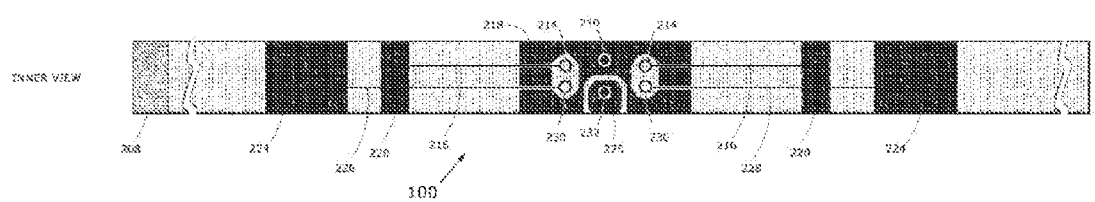

The present invention can be realized without dual use electrodes. In FIG. 2C and FIG. 2C', an alternate embodiment of the headgear of FIG. 2B and FIG. 2B' is shown that uses one set of EEG electrodes for EEG monitoring and a separate set of stimulation electrodes for electrical stimulation. This can reduce the surface area available for the electrical stimulation, but not by much if the EEG electrodes are kept sufficiently small. On the other hand, dual use electrodes require additional complexity in the electronics of the wearable dual use brain monitoring and stimulation device 300, so the embodiment shown in FIG. 2C and FIG. 2C' allows use of simpler electronic circuitry for the monitoring and stimulation.

In FIG. 2C and FIG. 2C', the EEG is monitored using three EEG electrodes: the frontal EEG electrode 226 and two lateral EEG electrodes 220. Each lateral EEG electrode 220 is connected by a lateral EEG wire 216 to a lateral EEG interface connector 214. The frontal EEG electrode 226 is connected to the frontal EEG interface connector 232 directly. Stimulation is delivered through three stimulation electrodes, larger in size than the EEG electrodes. The stimulation electrodes are the frontal stimulation electrode 218 and the lateral stimulation electrodes 224. Each lateral stimulation electrode 224 is connected by a lateral stimulation wire 228 to a lateral stimulation interface connector 230. The frontal stimulation electrode 218 is connected to the frontal stimulation interface connector 210 directly.

Figure 2D:
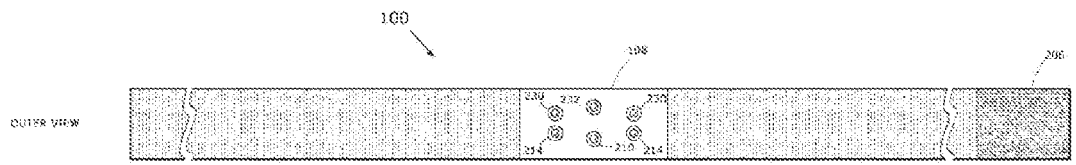
FIG. 2D and FIG. 2D' are schematic drawings of an alternate embodiment of the sleep wearable headgear of the invention, this embodiment including Ag—AgCl EEG electrodes.
Figure 2D:
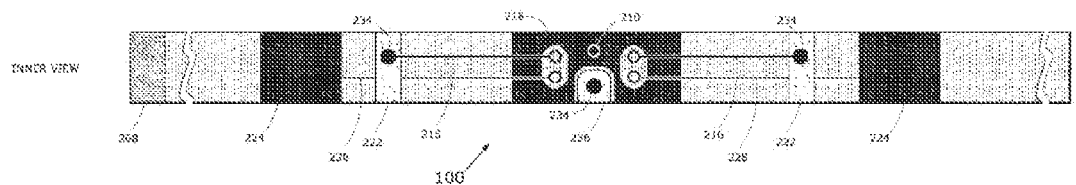

In FIG. 2D and FIG. 2D' another embodiment is illustrated, in which the EEG electrodes are Ag—AgCl electrodes. This type of electrode allows higher quality EEG recording. The frontal EEG Ag—AgCl electrode 236 and the lateral EEG Ag—AgCl electrodes 222 are connected in an identical way to FIG. 2C. They contain an Ag—AgCl element 234, covered by gel.

Alternate embodiments are possible, which utilize permutations of the variations described. Other possible variations include using interface connectors other than snap connectors, and using conductive textiles as electrodes. Conductive textiles however have higher impedances; this may be acceptable if the quality of the monitored EEG signal is less important than patient comfort, however conductive textiles available at the time of writing are normally not suited for stimulation. A stimulation electrode made with conductive textile material is possible but would require careful application of conductive EEG paste prior to sleep. Carbon nanotube electrodes and other electrodes based on nanostructures (still in development as of the time of writing) may soon be used for both EEG monitoring and stimulation, and require no conductive paste application.

Figure 3A:
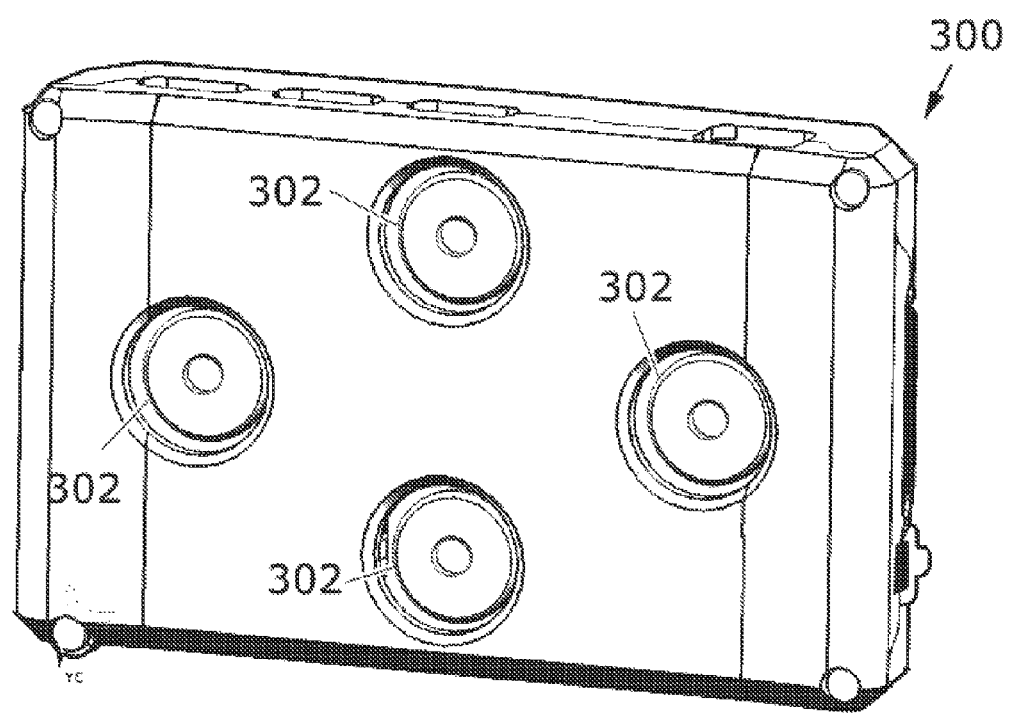
FIG. 3A is a line drawing of a wearable dual use brain monitoring and stimulation device suited for being connected to the embodiments of FIG. 2A and FIG. 2B of the sleep wearable headgear of the invention.
Figure 3B:
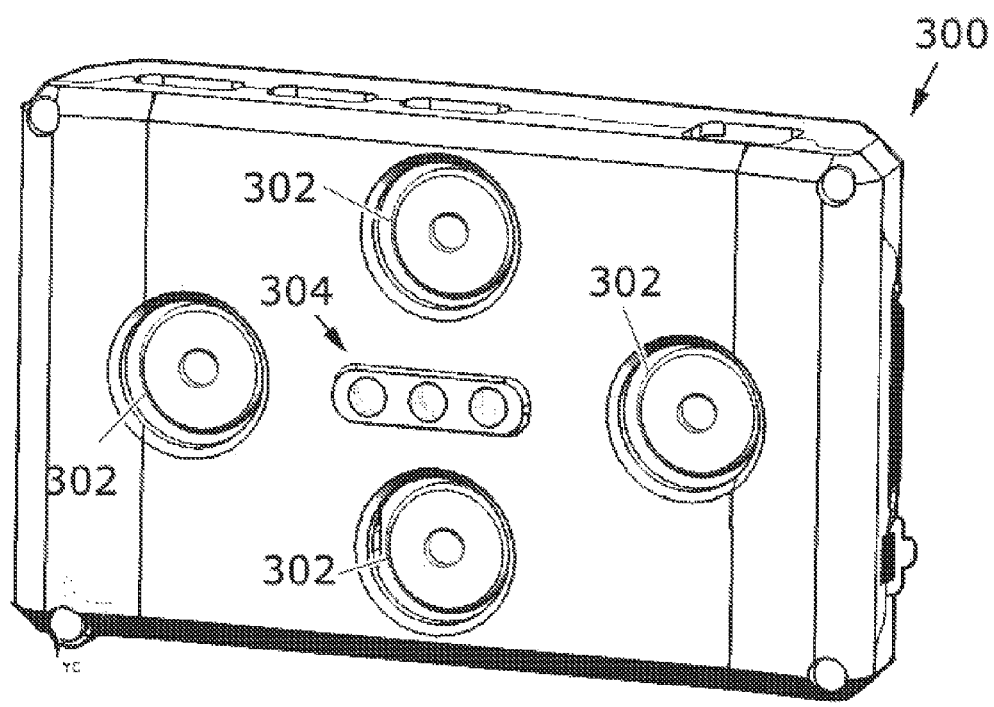
FIG. 3B is a line drawing of an alternate embodiment of the wearable dual use brain monitoring and stimulation device of FIG. 3A, this embodiment including a pulse oximetry sensor.

FIG. 3A shows a wearable dual use brain monitoring and stimulation device 300 suited for being connected to the headgears of FIG. 2A and FIG. 2B. Four female snap connectors 302 mate with the male snap connectors on the headgear (for instance, interface connectors 102, 104 in FIG. 2B and FIG. 2B'), providing structural and electrical connection. In FIG. 3B an alternative embodiment of the device 300 is shown that also includes a pulse oximetry sensor 304, whose position and size matches the hole 213 of FIG. 2B and FIG. 2B'. The pulse oximetry sensor 304 is can be used, for instance, to acquire the heart rate from the sleeping person 106. The heart rate can be used, for instance, to detect whether the person 106 is being adversely affected by the stimulation, and terminate the stimulation in response to any adverse reaction.

Figure 4:
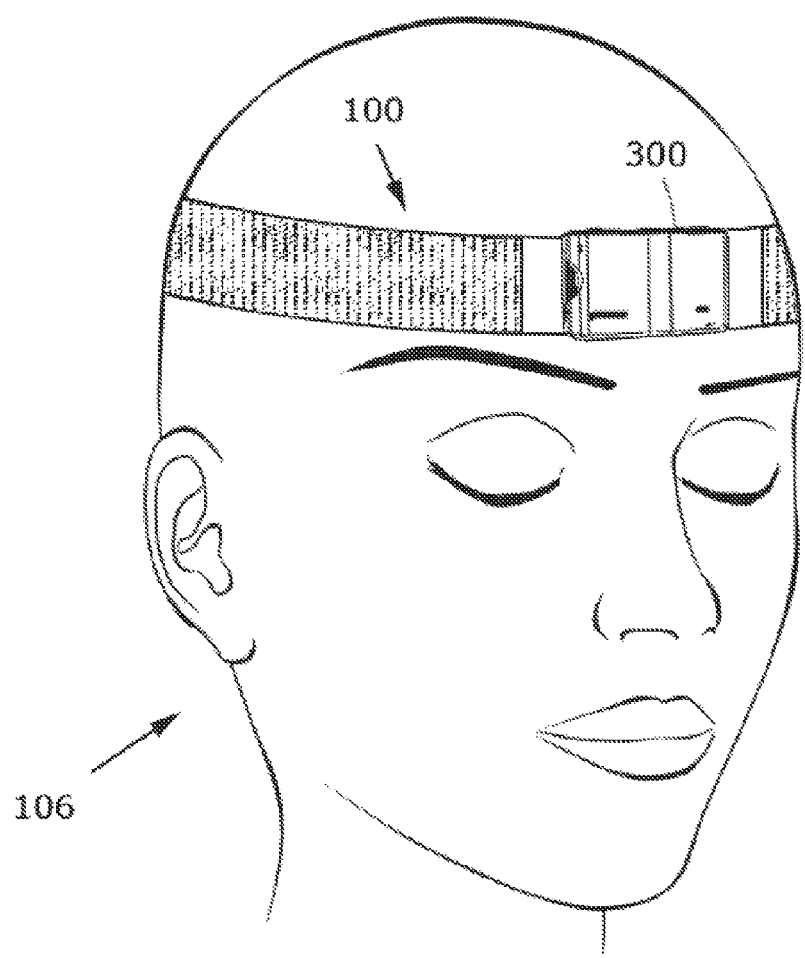
FIG. 4 is a line drawing of a person shown wearing the wearable dual use brain monitoring and stimulation device of FIG. 3A and FIG. 3B mounted on the headgear of FIG. 2A and FIG. 2B.

FIG. 4 shows the wearable dual use brain monitoring and stimulation device 300 of FIG. 3A and FIG. 3B mounted on the headgear 100 of FIG. 2A and FIG. 2B, and worn by a person 106.

Figure 5:
FIG. 5 is a line drawing of a person shown wearing an alternate embodiment of the headgear of the invention, this embodiment including multiple flexible bands and interface connectors located at the top of the person's head.

FIG. 5 shows a multi-band headgear 500 for both monitoring and stimulating the brain of a sleeping person 106. The multi-band headgear 500 has interface connectors 102, 104, 602 located at the top of the person's 106 head.

Figure 6:
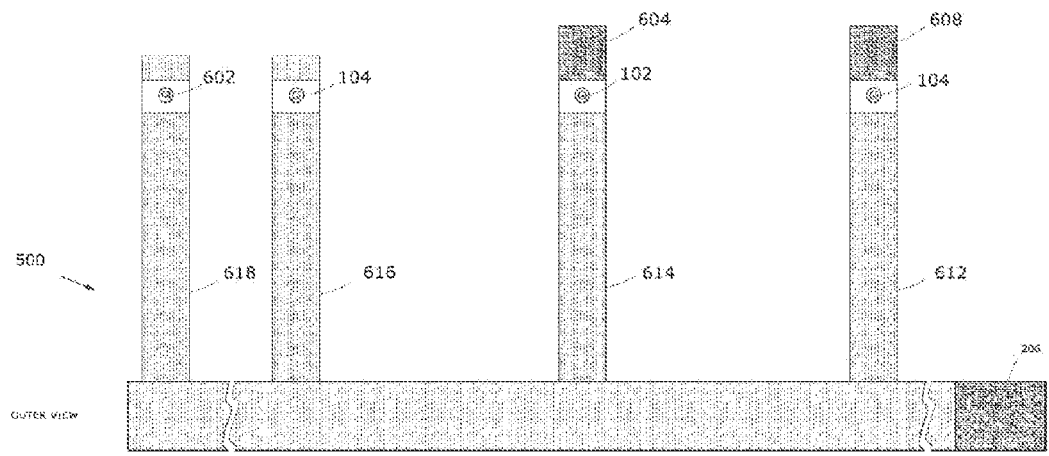
FIG. 6 and FIG. 6' are schematic drawings of an outer view and an inner view of the sleep wearable headgear of FIG. 5.
Figure 6:
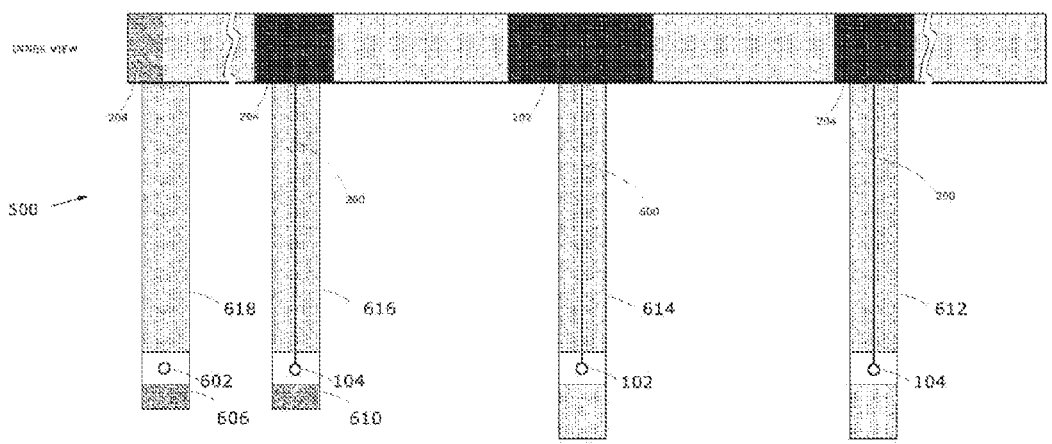

FIG. 6 and FIG. 6' show the details of a possible embodiment of the multi-band headgear 500 of FIG. 5, best understood in reference to the headgear 100 embodiment of FIG. 2A. A multi-band headgear allows a dual use monitoring and stimulation device to be secured to the top of the head. This is useful when the size of the device cannot be sufficiently miniaturized, or when forehead placement would interfere with some sleeping positions. The drawback is higher complexity, construction costs, and potential interference to the EEG signal resulting from the plurality of wires required.

In the multi-band headgear 500 of FIG. 6, the frontal dual use electrode 202 and lateral dual use electrodes 204 are positioned at locations on the person's 106 forehead at locations identical to FIGS. 2A, 2B, 2C, and 2D. Each lateral dual use electrode 204 is, as in FIG. 2A, electrically connected to a lateral interface connector 104 by a lateral wire 200. However, in FIG. 6 the lateral interface connectors 104 are located on the left support structure 612 and the right support structure 616. The frontal dual use electrode 202 is connected to a single frontal interface connector 102 by a frontal wire 600. The frontal interface connector 102 is located on the anterior support structure 614.

When worn, the multi-band headgear 500 is first secured around the head of the person 106 by the horizontal Velcro® loops 206 and horizontal Velcro® hooks 208. The anterior support structure 614 and the posterior support structure 618 are then joined by means of the anterior support structure Velcro® loops 604 and the posterior support structure Velcro® hooks 606. Similarly, the left support structure 612 is joined with the right support structure 616 by means of the left support structure Velcro® loops 608 and the right support structure Velcro® hooks 610, completing the assembly and capturing the person's 106 head.

In FIG. 6 and FIG. 6' one additional interface connector 602 on the rear support structure 618 is not electrically connected but provides symmetry and structural support.

Figure 7:
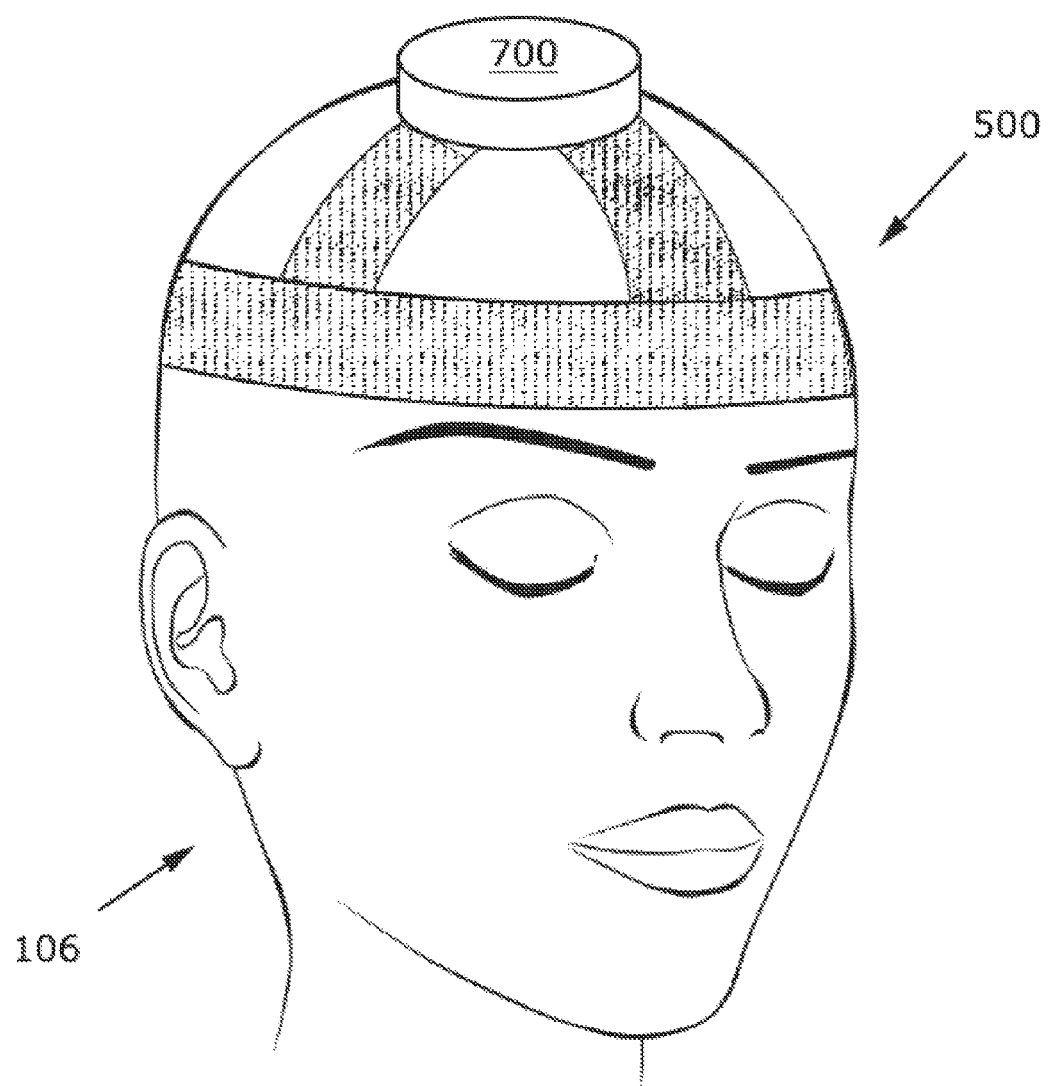
FIG. 7 is a line drawing of a person shown wearing a dual use brain monitoring and stimulation device, the device being attached to the headgear of FIG. 5.

FIG. 7 shows an over-the-head dual use brain monitoring and stimulation device 700, mated to the interface connectors of the multi-band headgear 500.

Figure 8:
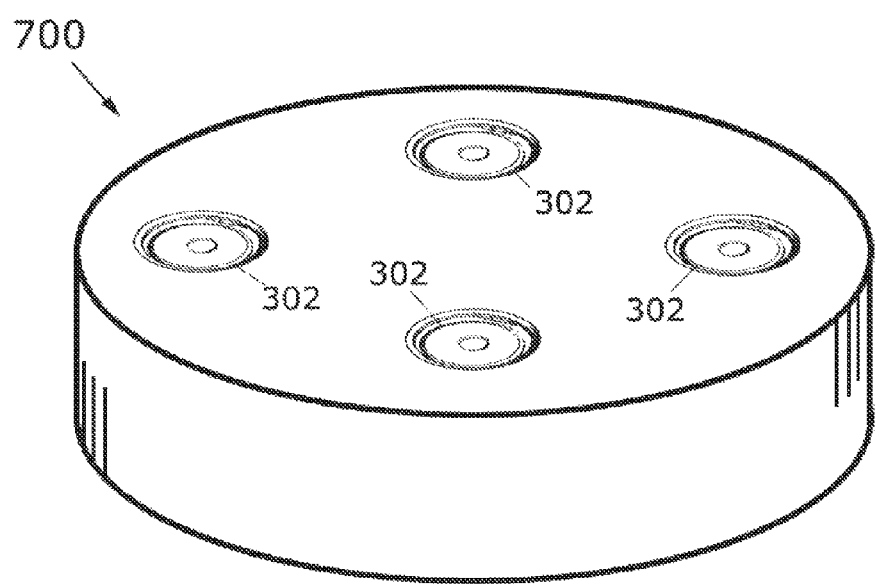
FIG. 8 is a line drawing of a bottom view of the dual use brain monitoring and stimulation device of FIG. 7

FIG. 8 shows the bottom side of the over-the-head dual use brain monitoring and stimulation device 700, and the female snap connectors 302 by which it is electrically and structurally connected to the multi-band headgear 500.

Figure 9:
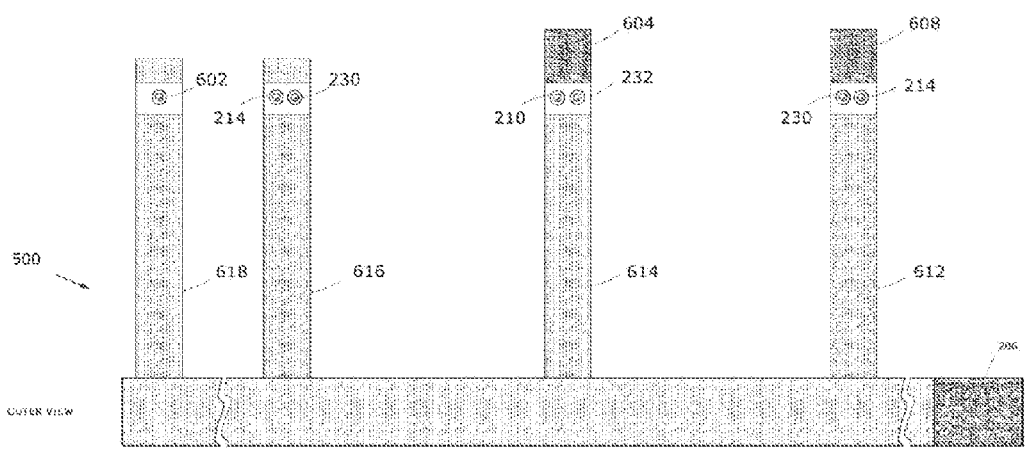
FIG. 9 and FIG. 9' are schematic drawings of an outer view and an inner view of an alternate embodiment of the headgear of FIG. 5, this embodiment including both EEG electrodes and stimulation electrodes.
Figure 9:
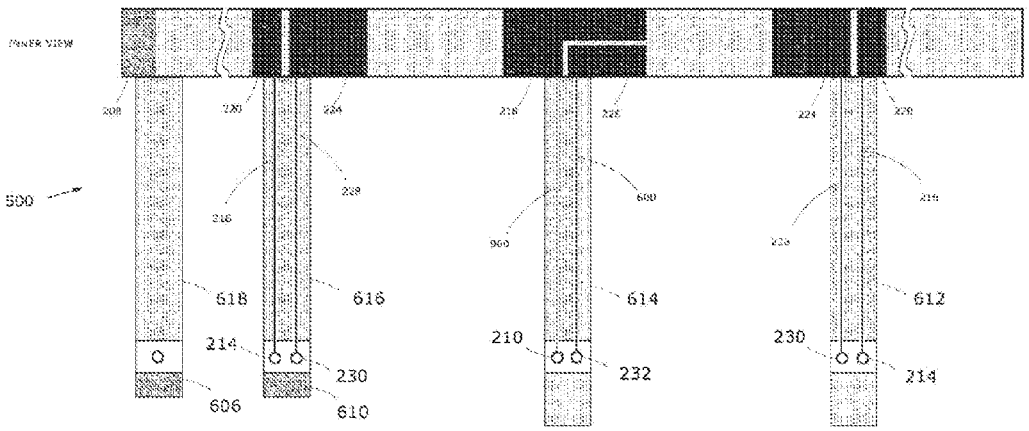

FIG. 9 and FIG. 9' show an alternate embodiment of the multi-band headgear 500. Like the headgear of FIG. 2B and FIG. 2B', this embodiment has two sets of electrodes, the electrodes used for EEG monitoring are smaller and the electrodes used for stimulation are larger. The frontal EEG electrode 226 is connected by a frontal EEG wire 600 to the frontal EEG interface connector 232. The frontal stimulation electrode 218 is connected by a frontal stimulation wire 900 to the frontal stimulation interface connector 210.

Figure 10:
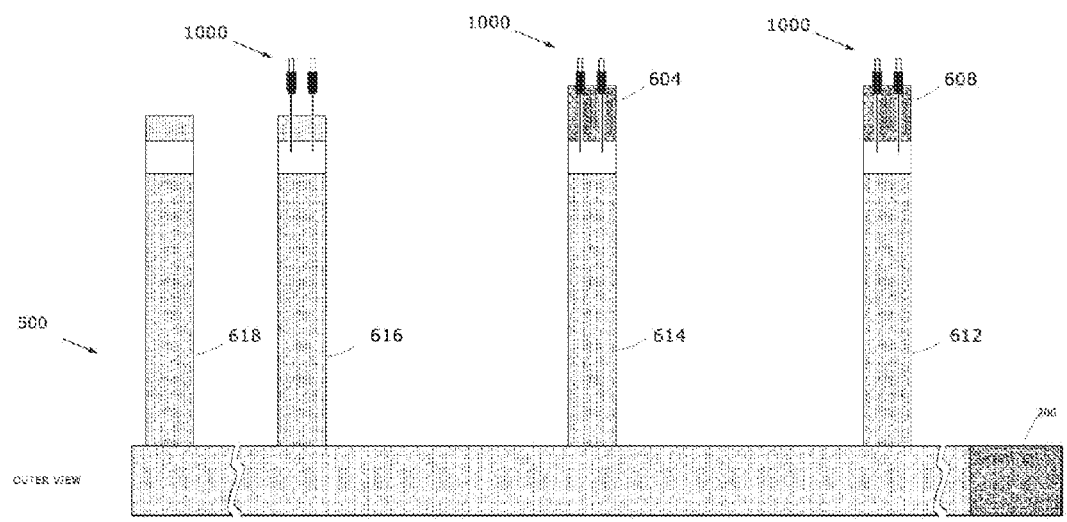
FIG. 10 and FIG. 10' are schematic drawings of an outer view and an inner view of an alternate embodiment of the headgear of FIG. 5, this embodiment being the same as the embodiment of FIG. 9 and FIG. 9', including banana plug connectors instead of snap connectors.
Figure 10:
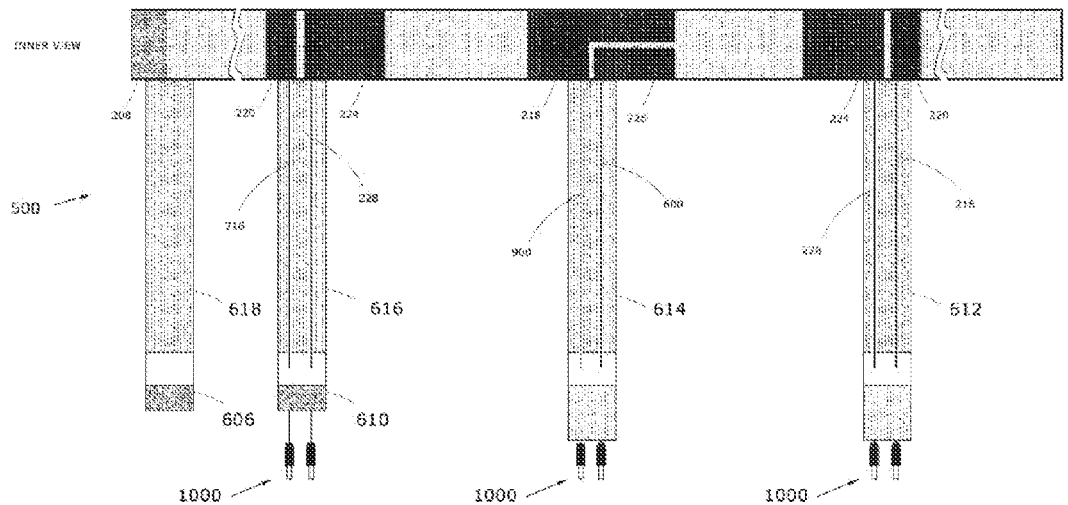

FIG. 10 and FIG. 10' show an alternative to the use of snap connectors as interface connectors. Here, the interface connectors are small banana plugs 1000 which can be plugged into a suitably modified over-the-head dual use brain monitoring and stimulation device 700, the device 700 having banana plug receptacles instead of female snap connectors 302. The plurality of banana plugs 1000 can provide sufficient structural support as well as electrical connectivity. Many more embodiments of the multi-band headgear 500 are possible; for instance, using Ag—AgCl electrodes as EEG electrodes, or modifying the number and shape of the support structures, or modifying the way in which the headgear is fastened to the head of the person 106.

Figure 11:
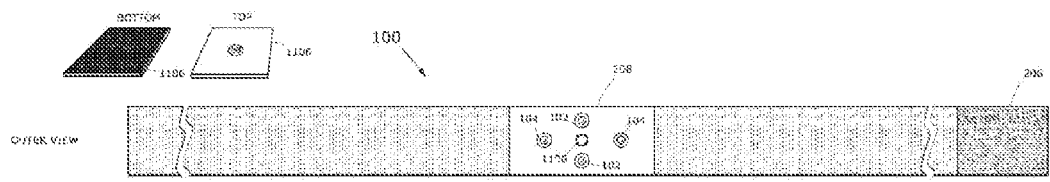
FIG. 11 and FIG. 11' are schematic drawings of an outer view and an inner view of an alternate embodiment of the headgear of FIG. 1, this embodiment including electrode connectors which allow the electrodes to be replaceable.
Figure 11:
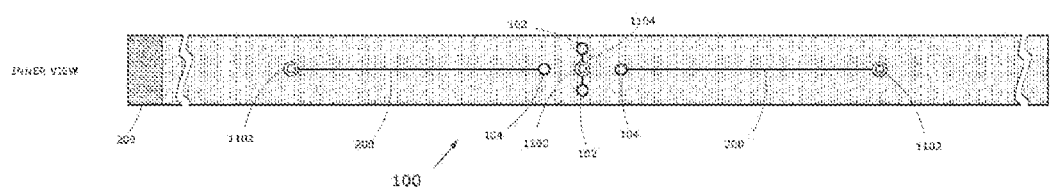

FIG. 11 and FIG. 11' show an alternative embodiment of the headgear 100 of FIG. 2A and FIG. 2A'. In this embodiment, the electrodes are replaceable and can be connected to electrode connectors 1102 located at predetermined locations along the headgear 100. By making the electrodes replaceable, the headgear does not need to be discarded when the electrodes wear out. All headgear embodiments shown in the figures can be modified to accept electrode connectors and replaceable electrodes. For simplicity, only the modification of the embodiment of FIG. 2A and FIG. 2A' is shown.

Snap prong connectors are—as explained earlier—composed of a top half and a bottom half. The headgear is captured between the two halves of each snap prong connector. In FIG. 11, three female snap prong connectors (one for each electrode) are incorporated into the headgear 100. A frontal electrode connector 1100 is located at the center of the headgear. Two lateral electrode connectors 1102 are laterally located. A lateral wire 200 connects each lateral electrode connector 1102 to the lateral interface connector 104. The frontal electrode connector 1100 is connected to the frontal interface connector 102 by a central wire 1104.

Suitably matching and properly sized disposable gel electrodes 1106 can now be connected to the electrode connectors on the headgear, and replaced when necessary.

The exact location and number of electrodes on the headgear depend on the purpose of the electrical stimulation. For example, if stimulation of only one brain hemisphere is required, one lateral electrode 204 and one wire 200 (and, optionally, one lateral interface connectors 104) can be removed. When the head of the person 106 has no hair, electrodes can also be located away from the forehead for both stimulation of underlying brain locations and EEG acquisition at the same locations.

Figure 12:
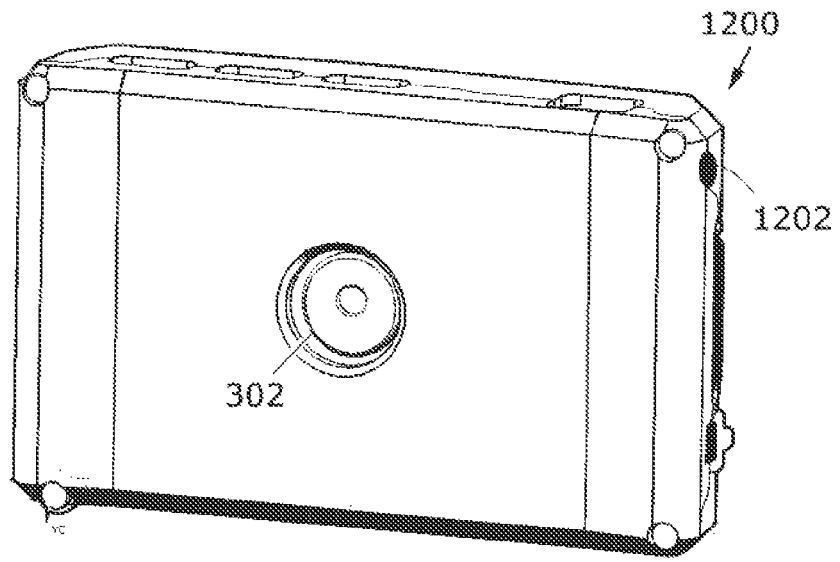
FIG. 12 is a line drawing of a minimal embodiment of the wearable dual use brain monitoring and stimulation device of FIG. 3A, the embodiment including a wire connector plug and only one female snap connector.

FIG. 12 shows a minimal embodiment 1200 of the wearable dual use brain monitoring and stimulation device, having a wire connector plug 1202 and only one female snap connector 302.

Figure 13:
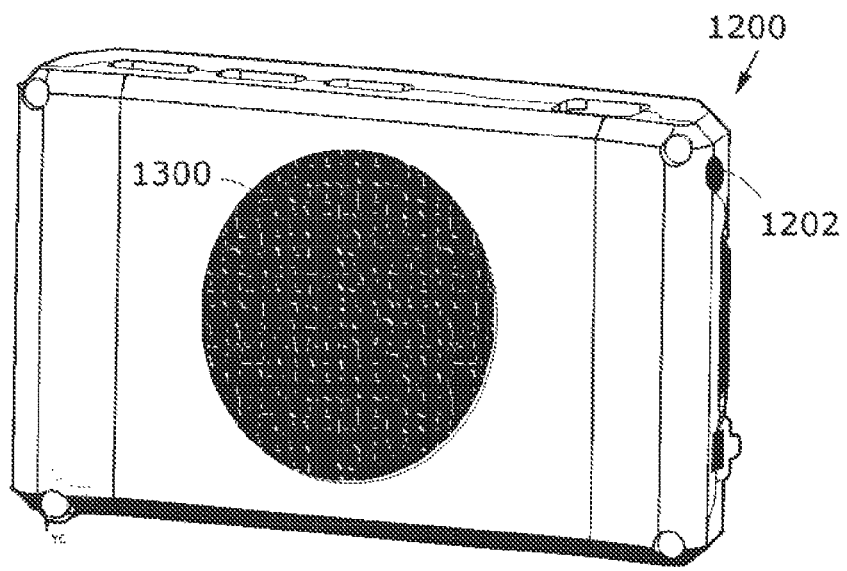
FIG. 13 is a line drawing of the dual use device of FIG. 12, showing one replaceable, dual use electrode connected to the dual use device of FIG. 12

FIG. 13 shows the dual use device 1200 with one replaceable, dual use device-mounted EEG and stimulation electrode 1300 connected.

Figure 14:
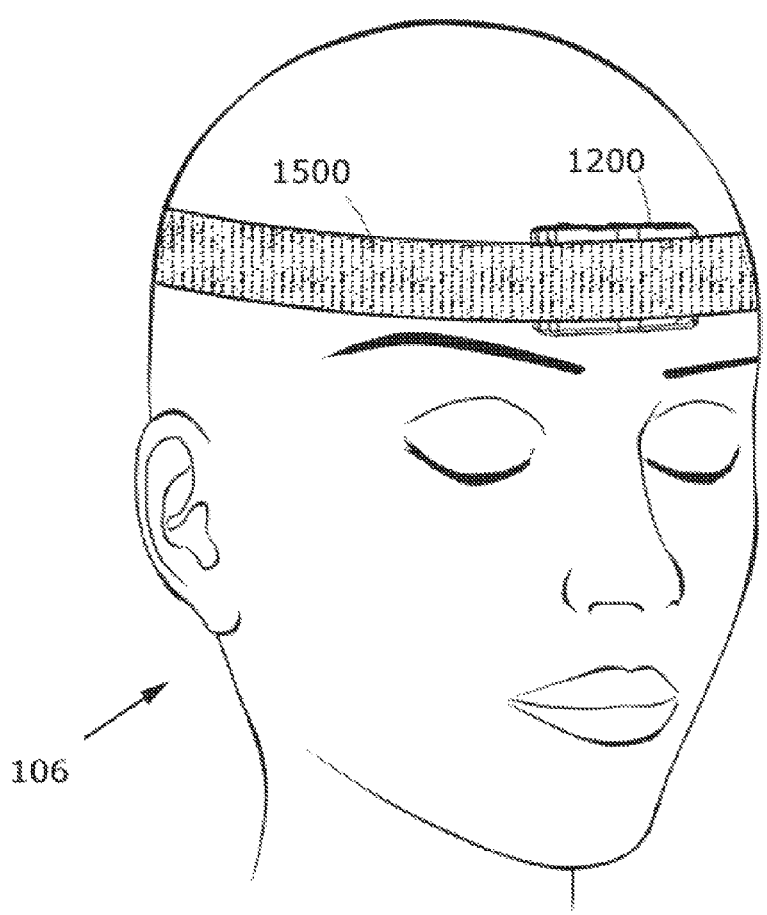
FIG. 14 is a line drawing of a person shown wearing the dual use device of FIG. 13, the dual use device being supported by a single-electrode, single-band headgear.

FIG. 14 shows the dual use device 1200 affixed to the person's 106 head, supported by a single-electrode, single-band headgear 1500.

Figure 15:
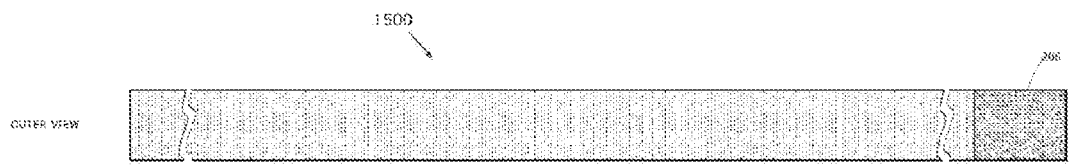
FIG. 15 and FIG. 15' are schematic drawings of an outer view and an inner view of the embodiment of FIG. 14, the embodiment including only one dual use headgear-mounted electrode.
Figure 15:
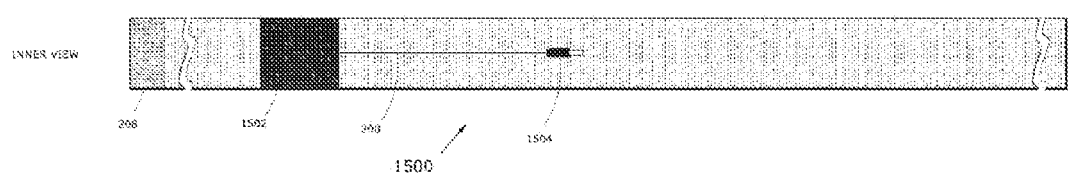

FIG. 15 and FIG. 15' show outer and inner views of the single-band headgear 1500, modified to have only one dual use headgear-mounted electrode 1502. This embodiment can be used in conjunction with the minimal embodiment 1200 of the wearable dual use brain monitoring and stimulation device. A single lateral interface connector wire 104 is plugged into the wire connector plug 1202 of the dual use device 1200. The dual use device 1200 is supported by the headgear 100. Two dual use electrodes are in contact with the person's 106 forehead: the device-mounted electrode 1300 and the headgear-mounted electrode 1502. Through these electrodes, the dual use device 1200 can perform EEG acquisition and electrical stimulation.

Figure 16:
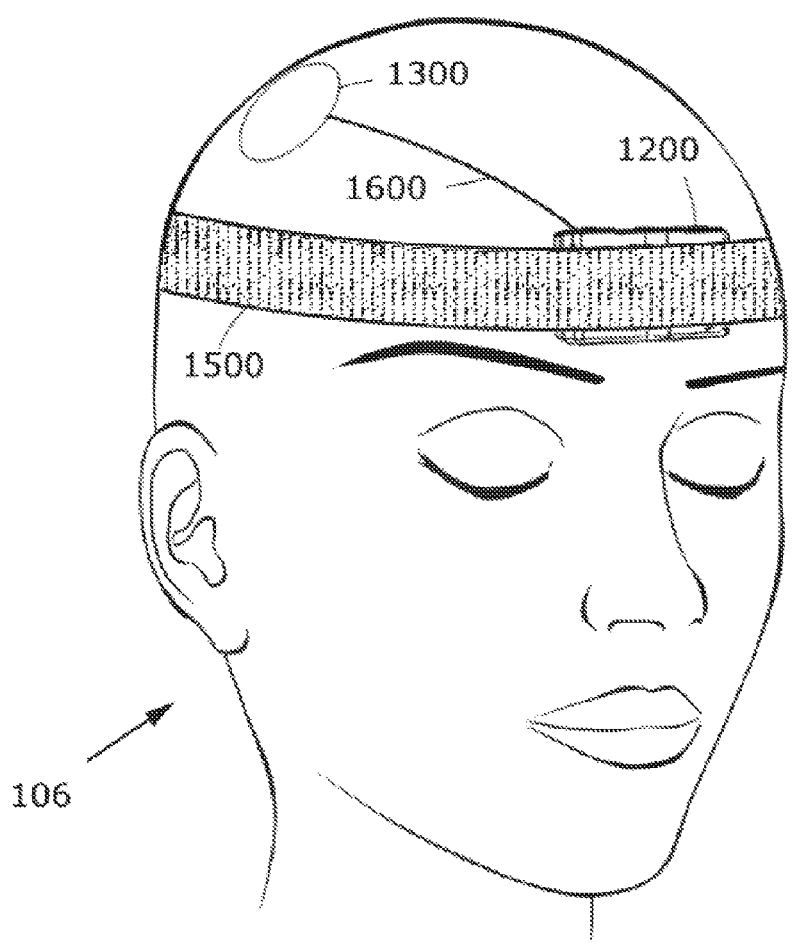
FIG. 16 is a line drawing of a person shown wearing an alternate embodiment of the dual use device of FIG. 13, this embodiment including a displaced electrode connected by a wire.

FIG. 16 shows an alternate embodiment of the minimal embodiment 1200 of the wearable dual use brain monitoring and stimulation device. In this embodiment, the device-mounted electrode 1300 is adhesive, and is affixed to a non-hairy portion of the head of the person 106. The device-mounted electrode 1300 is connected to the female snap connector 302 of the dual use device 1200 by a snap electrode wire 1600. In FIG. 16 the device-mounted electrode 1300 is located near the top of the person's 106 head, but it could also be located underneath the headgear 1500. Similarly, the headgear-mounted electrode 1502 could be central and located at the front of the headgear. Many more additional embodiments are possible, with additional device-mounted electrodes, or additional headgear-mounted electrodes. For instance, separate EEG electrodes and stimulation electrodes could be used instead of dual-use electrodes. A right leg drive electrode could be added. The permutations of previous embodiments, such as using electrode connectors, can apply.

Figure 17:
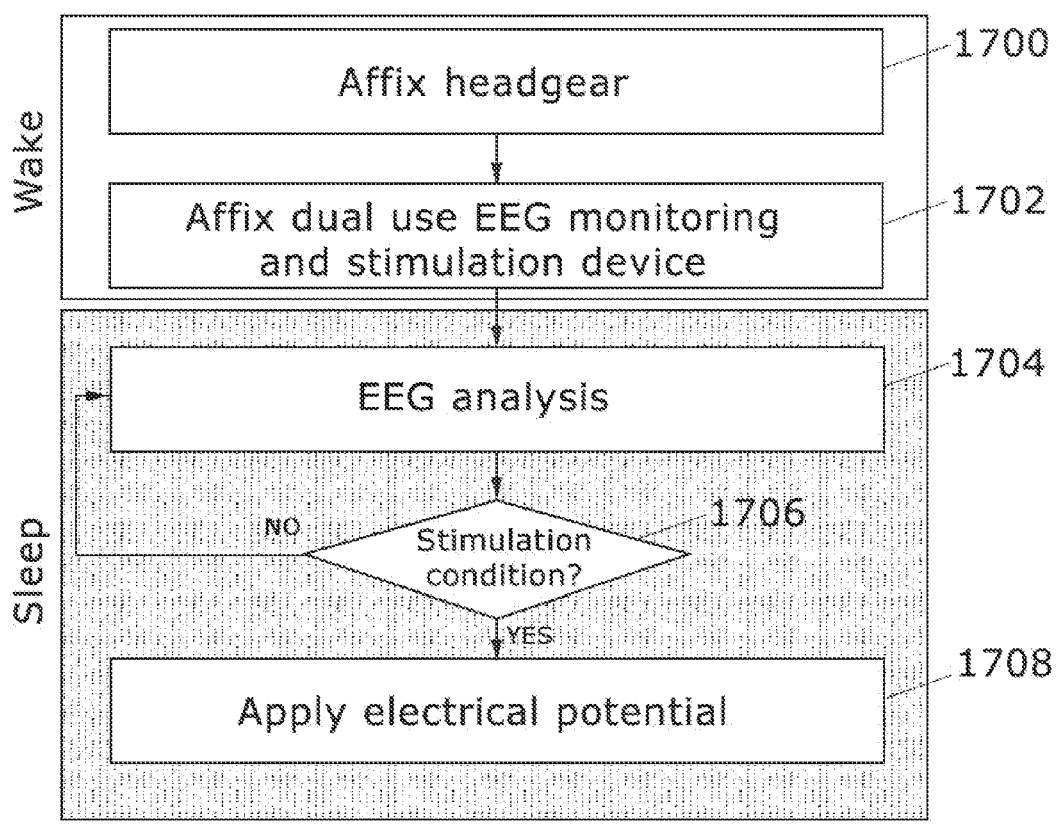
FIG. 17 is a flow chart of a process for stimulating the brain of a sleeping person.

FIG. 17 is a flow chart of a process for stimulating the brain of a sleeping person. The process includes two wake-time steps: the headgear wearing step 1700 and the dual use EEG monitoring and stimulation device connection step 1702. During the headgear wearing step 1700 a person wears a dual use EEG monitoring and stimulation headgear. During the dual use EEG monitoring and stimulation device connection step 1702 the person connects a dual use EEG monitoring and stimulation device to the headgear, creating electrical connections between the dual use device and the electrodes on the headgear.

The process also includes the following sleep-time phases. In the EEG analysis phase 1704 the EEG of the person is monitored for a predetermined interval, for example 10 seconds. During this phase the EEG is also analyzed so as to extract one or more features. Such features may include the fourier transform of the signal, which can be used to determine the sleep stage and the presence of frequency-specific EEG features such as sleep spindles; rapid eye movement contamination of the EEG signal, which can be used in conjunction to the fourier transform to determine whether the person is in REM sleep; and high frequency contamination of the signal, which can be caused by facial muscle tension or movement of the person and can be used to determine the degree of arousal.

In the stimulation condition detection step 1706 the acquired EEG features are used to detect a stimulation condition, such as the person entering REM sleep. The stimulation condition detection step 1706 may also include a time condition, so as to detect a stimulation condition only after the person has experienced a specific sleep phase for a certain amount of time. For instance, if a certain type of stimulation is to be carried out during REM sleep, it would be advisable for the stimulation to be started only after enough time has elapsed so as to allow multiple consecutive REM sleep detections. The stimulation condition detection could also be limited to a certain interval of time; for example one may wish to prevent stimulation during the first hours of sleep, and only detect a stimulation condition after a certain amount of time has elapsed. Or, one may want to restrict the stimulation condition detection to a predetermined time interval in the morning.

The stimulation condition detection step 1706 may also include a safety mechanism which prevents this step from detecting a stimulation condition if the impedance of the stimulation electrodes is too high to allow safe electrical stimulation of the person's brain. Measurement of electrode impedance can be easily carried out with the same electronic circuitry required to provide the electrical stimulation. To measure electrode impedance, a very small current of known intensity, too low to be perceived by the person, is delivered. The voltage across the electrodes is measured, and by Ohm's law the impedance is calculated.

When the stimulation condition detection step 1706 does not detect a stimulation condition, the EEG monitoring and analysis phase 1704 resumes, and another chunk of EEG data is acquired and analyzed. If the stimulation condition is detected, a stimulation phase 1708 is initiated. Termination of the stimulation phase 1708 can occur differently depending on the stimulation goal. Almost always the stimulation phase 1708 will terminate after a predetermined period of time has elapsed. One may also want to monitor the person's vital signs, such as the heart rate or breathing rate, so as to detect an unwanted harmful effect of the stimulation, and then promptly terminate the stimulation.

Once the stimulation phase 1708 has ended, the process can end as shown in FIG. 17 with no further stimulations; or, the EEG analysis phase 1704 could begin again. When the process is cyclical and multiple stimulation phases 1708 can occur, one may want to prevent excessive stimulation by means of a timeout, preventing the stimulation condition detection step 1706 from detecting a stimulation condition for a predetermined amount of time (for example, half an hour) after the previous stimulation phase 1708.

Figure 18:
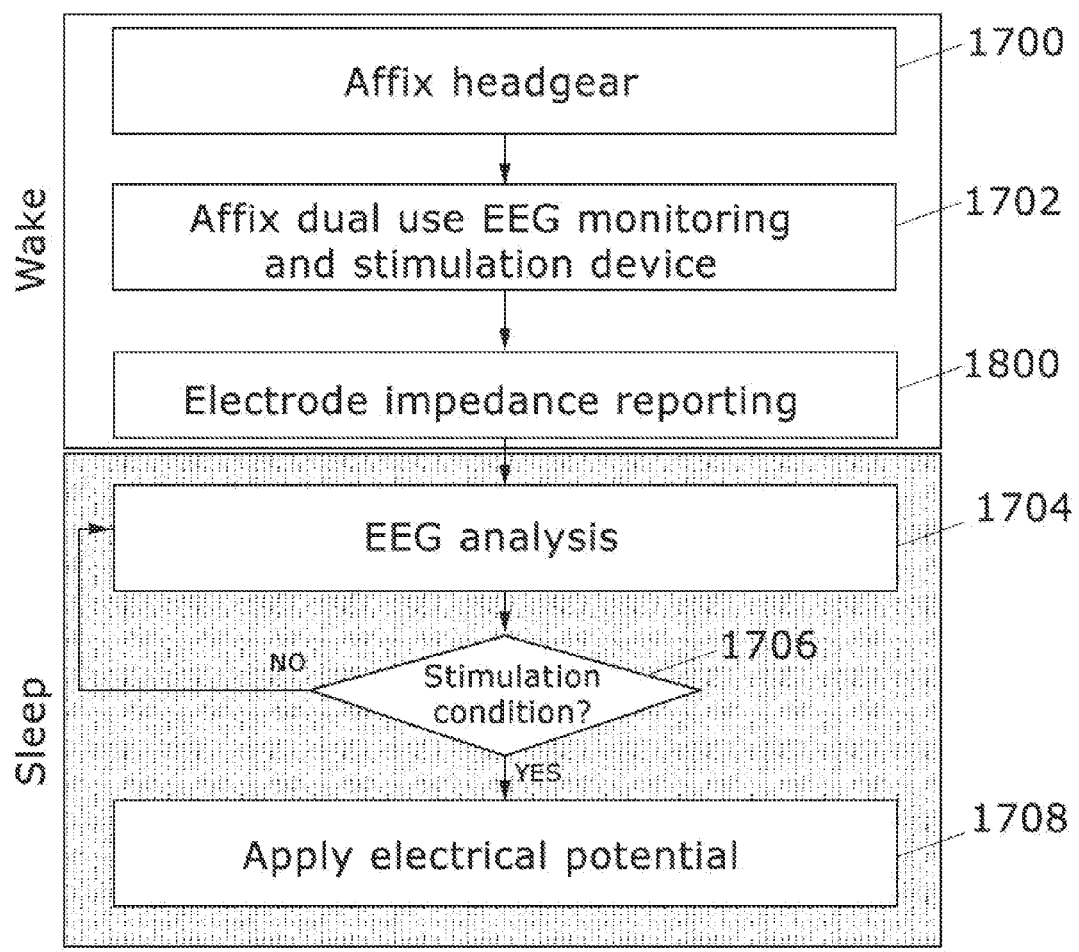
FIG. 18 is a flow chart of an alternate embodiment of the process of FIG. 17, the embodiment also including an electrode impedance reporting step.

FIG. 18 is a flow chart for an alternate embodiment of the process of FIG. 17, the embodiment also including an electrode impedance reporting step 1800. During the electrode impedance reporting step 1800, the person receives a visual or auditory report from the dual use EEG monitoring and stimulation device (or a mobile device capable of interfacing with to the dual use EEG monitoring and stimulation device). The report can be a simple pass/fail report, possibly in the form of a red or green colored light delivered by an LED mounted on the dual use device, or an easily recognizable pass/fail auditory signal. Alternatively, the report can communicate a measure of the impedance of the electrodes, such as a value in ohms displayed on the screen of a mobile phone, the mobile phone wirelessly receiving impedance data from the dual use device. If the electrode impedance is too high, the user can adjust the headgear, add conductive paste under the electrodes, or add water to the electrodes if the electrodes are sponges. When the electrode impedance is sufficiently low to allow safely stimulating the brain of the person during sleep, the user receives a "pass" report, and then begins the process of falling asleep. As the person falls asleep, the process moves forward to the EEG analysis phase.

Other modifications and implementations will occur to those skilled in the art without departing from the spirit and the scope of the invention as claimed. Accordingly, the above description is not intended to limit the invention except as indicated in the following claims.

What is claimed is:

1. A dual purpose sleep wearable headgear for both monitoring and stimulating the brain of a sleeping person, the headgear comprising:
   one or more flexible bands capable of being worn so as to capture the head of the sleeping person, one of the flexible bands wearable over the forehead of the sleeping person;
   a plurality of electrodes, each electrode including an Ag—AgCl element covered by gel, at least some of the electrodes being sized and located along the flexible band wearable over the forehead so as to be capable of applying electrical stimulation to the sleeping person's brain, at least some of the plurality of electrodes also being capable of acquiring an EEG signal;
   a plurality of electrode connectors located along the flexible band wearable over the forehead, capable of receiving the plurality of electrodes,
   each electrode connector being incorporated into the flexible band wearable over the forehead so as to direct the electrical stimulation to an underlying portion of the sleeping person's brain;
   an enclosure capable of enclosing a wearable dual use brain monitoring and stimulation device having an electronic circuit for both acquiring the EEG signal and applying the electrical stimulation; and
   a plurality of interface connectors for electrically connecting the electronic circuit to the headgear, the electronic circuit being capable of both acquiring the EEG signal and applying the electrical stimulation, each interface connector being electrically connected to at least one of the plurality of electrode connectors.

2. The headgear of claim 1, wherein some interface connectors are electrically connected to at least one of the plurality of electrode connectors using one of: a wire; or a conductive fabric strip; or a conductive thread; and or a flexible circuit board.

3. The headgear of claim 1, wherein at least one of the plurality of interface connectors is one of: an electrical snap connector; or a piece of conductive hook and loop material; or a magnet.

4. The headgear of claim 1, wherein at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

5. A dual purpose sleep wearable headgear for both monitoring and stimulating the brain of a sleeping person, the headgear comprising:
   one or more flexible bands capable of being worn so as to capture the head of the sleeping person, one of the flexible bands wearable over the forehead of the sleeping person;
   a plurality of electrodes, including an Ag—AgCl element covered by gel, at least some of the electrodes being sized and located along the flexible band wearable over the forehead so as to be capable of applying electrical stimulation to the sleeping person's brain, at least some of the plurality of electrodes also being capable of acquiring an EEG signal, each electrode being incorporated into the flexible band wearable over the forehead so as to direct the electrical stimulation to an underlying portion of the sleeping person's brain;

an enclosure capable of enclosing a wearable dual use brain monitoring and stimulation device having an electronic circuit for both acquiring the EEG signal and applying the electrical stimulation; and a plurality of interface connectors for electrically connecting the electronic circuit to the headgear, the electronic circuit being capable of both acquiring the EEG signal and applying the electrical stimulation, each interface connector being electrically connected to at least one of the plurality of electrode connectors.

6. The headgear of claim 5, wherein some interface connectors are electrically connected to at least one of the plurality of electrode connectors using one of: a wire; a conductive fabric strip; a conductive thread; and a flexible circuit board.

7. The headgear of claim 5, wherein at least one of the plurality of interface connectors is one of: an electrical snap connector; or a piece of conductive hook and loop material; or a magnet.

8. The headgear of claim 5, wherein at least one of the one or more flexible bands is capable of structurally supporting the bulk of an enclosure enclosing the electronic circuit, so as to support the enclosure at a predetermined position on the sleeping person's head, the predetermined position selected so as to avoid substantially interfering with the sleeping person's sleep.

9. A method for stimulating the brain of a sleeping person, the method comprising:

affixing a flexible, sleep wearable band to the head of the sleeping person, the band having a plurality of electrodes, said electrodes being covered by gel and located so as to be automatically positioned along the forehead of the sleeping person, attaching a dual use EEG monitoring and stimulation device to the sleep wearable band, so that the dual use EEG monitoring and stimulation device is mechanically secured to and fully supported by the sleep wearable band, as well as electrically connected to the plurality of electrodes analyzing the EEG of the sleeping person's brain so as to detect a stimulation start condition, and applying an electrical potential to two or more of the plurality of electrodes, so as to deliver an electrical current to the sleeping person's brain in response to the stimulation start condition.

10. The method of claim 9, wherein the stimulation signal condition is one of: a sleep phase; a period of time after entering a sleep phase; and a sleep EEG feature as in a sleep spindle.

11. The method of claim 9, wherein the electrode potential is variable, so as to deliver a time-variable electrical current to the sleeping person's brain in response to the stimulation start condition, the time-variable electrical current being one of: an alternating current, or a random noise electrical current.

12. The method of claim 9, wherein the magnitude of the electrical current is increased gradually so as to reduce discomfort and to avoid disturbing the person's sleep.

13. The method of claim 9, wherein the electrical current is delivered so as to induce a lucid dream.

14. The method of claim 9, wherein the electrical current is an alternating current of a frequency between 30 and 50 hertz.

15. The method of claim 9, also comprising:

an electrode impedance reporting phase after the attaching a dual use EEG monitoring and stimulation device to the sleep wearable headgear, so as to allow the person to adjust the headgear or add conductive paste to the headgear's electrodes until the electrode impedance is sufficiently low for stimulation to occur safely.

16. The method of claim 9, wherein the stimulation start condition is not permitted to proceed when the impedance of the stimulation electrodes is too high for stimulation to occur safely.

* * * * *